(12) United States Patent
Fisher

(10) Patent No.: US 7,972,619 B2
(45) Date of Patent: *Jul. 5, 2011

(54) BIODEGRADABLE POLYMER FOR MARKING TISSUE AND SEALING TRACTS

(75) Inventor: John S. Fisher, Belleair, FL (US)

(73) Assignee: Biopsy Sciences, LLC, Clearwater, FL (US)

( * ) Notice: Subject to any disclaimer, the term of this patent is extended or adjusted under 35 U.S.C. 154(b) by 1042 days.

This patent is subject to a terminal disclaimer.

(21) Appl. No.: 11/784,310

(22) Filed: Apr. 6, 2007

(65) Prior Publication Data

US 2008/0161848 A1 Jul. 3, 2008

Related U.S. Application Data

(63) Continuation of application No. 10/063,620, filed on May 3, 2002, now Pat. No. 7,329,414.

(51) Int. Cl.
*A61L 15/16* (2006.01)
(52) U.S. Cl. ........................................ 424/444
(58) Field of Classification Search .................... None
See application file for complete search history.

(56) References Cited

U.S. PATENT DOCUMENTS

| | | | |
|---|---|---|---|
| 5,410,016 | A | 4/1995 | Hubbell et al. |
| 6,060,582 | A | 5/2000 | Hubbell et al. |
| 6,083,524 | A | 7/2000 | Sawhney et al. |
| 6,177,095 | B1 | 1/2001 | Sawhney et al. |
| 6,306,922 | B1 | 10/2001 | Hubbell et al. |
| 6,350,244 | B1 | 2/2002 | Fisher |
| 6,592,608 | B2 | 7/2003 | Fisher et al. |
| 6,602,975 | B2 | 8/2003 | Hubbell et al. |
| 6,605,294 | B2 | 8/2003 | Sawhney |
| 6,685,727 | B2 | 2/2004 | Fisher et al. |
| 6,887,974 | B2 | 5/2005 | Pathak |
| 7,001,410 | B2 | 2/2006 | Fisher et al. |
| 7,329,414 | B2 * | 2/2008 | Fisher et al. ............... 424/426 |
| 2004/0009205 | A1 | 1/2004 | Sawhney |
| 2004/0030262 | A1 | 2/2004 | Fisher et al. |
| 2006/0034930 | A1 | 2/2006 | Khosravi et al. |
| 2006/0100664 | A1 | 5/2006 | Pai et al. |
| 2006/0193899 | A1 | 8/2006 | Sawhney |

FOREIGN PATENT DOCUMENTS
WO WO 03/093338 11/2003

OTHER PUBLICATIONS

Langlois et al., "Carbon Localization of Impalpable Mammographic Abnormalities," Australas Radiol., (1991), pp. 237-241, vol. 35.
Svane, "Stereotaxic Technique for Preoperative Marking of Non-Palpable Breast Lesions," Acta Radiol. Diagnosis, (1983), pp. 145-151, vol. 24, No. 2.

* cited by examiner

*Primary Examiner* — Carlos A Azpuru
(74) *Attorney, Agent, or Firm* — Marshall, Gerstein & Borun LLP

(57) ABSTRACT

A tissue marker formed of a biodegradable polymer having drug-delivery capabilities is combined with a sealant that encapsulates the tissue marker and which serves to help anchor the tissue marker against migration. The sealant is delivered to a site in dehydrated form and moisture inherent in tissue at the site expands the sealant. The expanded sealant is formed of a hydrogel and is therefore more compatible to the surrounding tissue than the material of the tissue marker. The sealant and the tissue marker are both bioabsorbed over time.

9 Claims, 7 Drawing Sheets

FIG. 14
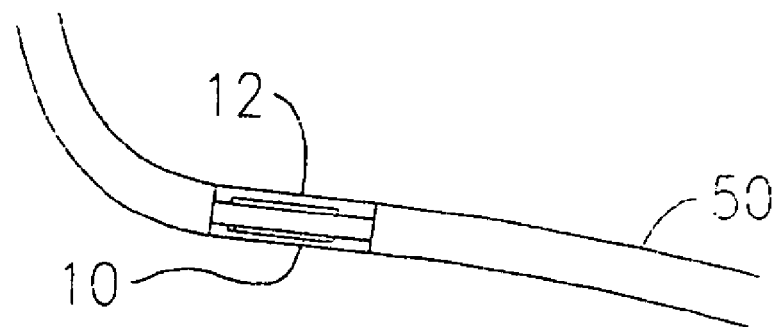
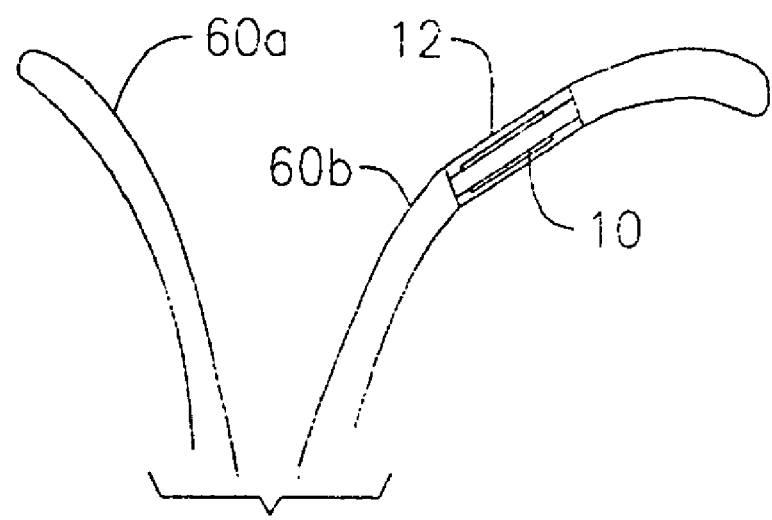
FIG. 15

BIODEGRADABLE POLYMER FOR MARKING TISSUE AND SEALING TRACTS

CROSS REFERENCE TO RELATED APPLICATIONS

This is a continuation of U.S. application Ser. No. 10/063,620, filed May 3, 2002.

BACKGROUND OF INVENTION

1. Field of the Invention

This invention relates, generally, to a biodegradable tissue marker and sealant. More particularly, it relates to a tissue marker formed of a biodegradable polymer having drug-delivery capabilities. It further relates to a sealant that encapsulates the tissue marker and which serves to help anchor the tissue marker against migration.

2. Description of the Prior Art

U.S. Pat. No. 6,350,244 entitled Bioabsorable Markers For Use In Biopsy Procedures to the present inventor discloses a bioabsorbable marker that is positioned near a lesion or tumor during a biopsy procedure. The marker includes a contrast agent and is bioabsorbed slowly so that the biopsy site can be located weeks or even months later if needed. U.S. Pat. No. 6,350,244 is hereby incorporated by reference into this disclosure, and is hereinafter referred to as the first-incorporated patent.

Co-pending U.S. patent application Ser. No. 09/683,282, filed Dec. 7, 2001, entitled Bioabsorbable Sealant, also to the present inventor, discloses a sealant that expands upon contact with water or other bodily fluid. It can also expand upon contact with heat or other stimulus. The sealant has utility in sealing various openings in the body such as a hole in a lung, an opening in the myocardial septum, and the like. It is also useful in sealing a blind bore that contains stem cells that promote angiogenesis. U.S. patent application Ser. No. 09/683,282 is also hereby incorporated by reference into this disclosure, and is hereinafter referred to as the second-incorporated disclosure.

Prior to this disclosure, it was not known that the tissue marker of the first-incorporated disclosure and the sealant of the second incorporated disclosure could be combined and used in combination with one another. Anchoring the tissue marker against migration was problematic. Moreover, although the tissue marker included a contrast solution to facilitate its imaging under X-rays, it was unknown how to use the tissue marker or the sealant as a drug delivery means.

Nor was it known that a tissue marker could be formed into a shape that would enable it to serve as its own anchoring means.

Nor was it known how polymers having utility as tissue markers could be formulated to achieve differing degradation rates. More particularly, it was not known how to make different polymers to contain contrast for different amounts of time, such as one month to six months or more by using two different polymers.

Nor was it known how to formulate a marker polymer with a therapeutic drug or other pharmaceutical agent so that the degradation of the marker would gradually release the drug or agent to a site.

Nor was it known how the polymers could be formulated to exhibit differing expansion rates when exposed to water or other liquid fluids.

The sealants of the prior art require in-situ curing. For example, Focal Sealant® is an in-situ sealant available from Genzyme Corporation. Prior art sealants such as Focal Sealant require the application of a stimulant such as visible light, heat, and the like thereto.

Accordingly, what is needed is a combination tissue marker and sealant that can be formed into many different shapes and sizes, depending upon the application, that can degrade at different rates, depending upon the application, that can expand in response to moisture or other bodily fluids at different rates, depending upon the application, and that does not require in-situ curing.

There is a need as well for a bioabsorbable tissue marker that can deliver drugs or other therapeutic agents to a site over a prolonged period of time.

There is a further need for a sealant that can anchor a tissue marker against migration, that can provide a seal for openings in tissue, and that biodegrades over a period of one to six months or more.

Moreover, there is a need for a combination tissue marker and sealant that requires no in-situ curing as aforesaid and which therefore requires no initiators, buffers or other chemicals, proteins, enzymes, visible light, UV, accelerator, nor addition of foreign chemicals into the body.

A need also exists for a means for making tissue markers more compatible with surrounding tissue. Tissue markers are hard and have little compatibility with surrounding tissue. Thus there is a need for a cushioning means that surrounds a marker and which provides a more compatible interface means with surrounding tissue.

Biodegradable polymers in general have been used in many medical devices and implant applications. For example, they have been used as orthopedic implants, tissue sealants, sutures, and as ligating clips. The medical devices incorporating these polymers are made, primarily, of biodegradable materials such as poly(dioxanone) (PDO), polyethylene glycol (hydrogels, polylactides (PLA), polyglycolides (PGA), polycaprolactone (PCL), and their copolymers. Some of the polymers, such as hydrogels, are hydrophilic. Others such as PCL are hydrophobic. Because these polymers degrade by hydrolysis, the type of polymer and its physical form used in a particular application has an effect in defining the degradation period.

Traditional brain tumor treatment includes surgery, radiotherapy, and chemotherapy. Alternative strategies are needed due to the high rate of recurrence of tumors after such treatment and their resistance to radiation and cytostatics. In the recent past, gene therapy treatments such as reversion of the malignant phenotype by down regulation of the oncogene expression or insertion of normal tumor genes have been tried. One challenge with gene therapy treatments concerns the prevention of immunorejection of genetically modified cells after intracranial implantation. A further challenge is to achieve efficient gene transfer, as well as prolonged gene expression within the relevant cells.

Numerous other surgical procedures would be facilitated by tissue markers that degrade over predetermined periods of time, that include contrast agents so that they can easily be found, that do not migrate, that interface well with surrounding tissue, and that deliver drugs or other therapeutic agents to a site over a predetermined length of time.

In view of the prior art considered as a whole at the time the present invention made, it was not obvious to those of ordinary skill in the pertinent art how the identified needs could be fulfilled.

SUMMARY OF INVENTION

Biodegradable polymers and co-polymers are combined with or without ionic and non-ionic contrast agents, depending upon the application. For example, no contrast agent is needed in an application where there is no need to view a site at a later date.

The novel formulations that include contrast agents are designed to allow the radiopacity of the markers to last for an extended period of time so that they can be seen under X-ray or other imaging means for further diagnostic or intervention procedures at a date that may be weeks or months after implanting of the marker.

The novel plug is treated so that it is visible under ultrasound, magnetic resonance imaging, and other imaging techniques if an application requires such visibility. Accordingly, it may contain or be impregnated with a contrast solution containing radium, iodine, beryllium, or other contrasting agent.

The plug is impregnated with a contrasting agent to facilitate detection of the plug by imaging means selected from the group of imaging, means consisting of magnetic resonance imaging, ultrasound, Doppler, and roentgenological means including x-ray, computed axial tomography (CAT) scanning, also known as CT scan, mammography, and fluoroscopy, or other known or hereafter known imaging techniques.

The plug may also include a radioactive substance detectable by a radiation detecting means including a gamma counter and a scintillation counter. In another alternative, the plug includes a transmitting means adapted to transmit signals in the electromagnetic spectrum that are detectable by receivers adapted to receive signals in the electromagnetic spectrum.

The novel polymers are based upon well-known polymers such as polyactides (PLA), including polylactic acid, for example, polyglycolides (PGA), including polyglycolic acid, for example, polycaprolactone (PCL), poly(dioxanone) (PDO), collagen, renatured collagen, gelatin, renatured gelatin, crosslinked gelatin, and their co-polymers. The blend of polymers and copolymers is designed to degrade as a result of hydrolysis of polymer chains into biologically acceptable and progressively smaller components such as polylactides, polyglycolides, and their copolymers. These break down eventually into lactic and glycolic acid, enter the Kreb's cycle and are broken down into carbon dioxide and water and excreted.

Some of these polymers and copolymers do not possess the mechanical properties that are required for certain applications. For example, as implants for soft tissue PGA, PLA, PCL, PDO and their copolymers may require increased flexibility and a modulus of elasticity that is closer to soft tissue. Some hydrogels, due to their water content, provide a more flexible structure that is similar to soft tissue. Therefore, by combining the polymers that lack certain required mechanical properties such as a suitable modulus of rigidity or modulus of elasticity with hydrogels, suitable degradation and drug delivery properties are obtainable and an exterior is achieved that has mechanical properties similar to the mechanical properties of soft tissue.

PLA, PGA, PCL, PDO and their copolymers are designed to provide a sustainable and gradual degradation and therefore slow release of drugs with the degradation of the polymer substrate. Hydrogels are not suitable for prolonged drug delivery without using additional bonding of the drug to the hydrogels especially with small size molecule pharmaceutical agents.

Thus it is understood that a primary teaching of this invention relates to biodegradable polymers having utility as tissue markers as taught by the first-incorporated patent and as sealants as taught by the second-incorporated disclosure. When combined, the tissue marker and sealant serve as a drug-delivery means as the substrate of the polymer degrades. Advantageously, the expanded sealant prevents migration of the marker as well, and provides a soft interface means between the marker and surrounding soft tissue.

More particularly, poly (DL-lactide) is used to provide a biodegradable substrate that allows slow degradation. However, it swells as water or other bodily fluid penetrates into the substrate. Different molecular weights could be used to achieve a different hydration rate. Delayed hydration provides a better visualization under ultrasound when further diagnosis or intervention is required.

An alternative method for achieving a different degradation rate is to employ a biodegradable hydrophobic polymer coating to delay the penetration into the substrate by water or other bodily fluid. The hydrophobic coating may be sprayed onto the substrate or the substrate may be dipped into the coating. Either way, the thickness of the coating is controlled because a thicker coating resists penetration for a longer time than a thinner coating. Polycaprolactone (PCL) degrades nicely, for example, and therefore works well when sprayed or coated onto the substrate. Teflon® does not work because it forms a substantially permanent shield.

When anchoring an implant in a specific area is required, a PGA/PLA/PCL/PDO based polymer combined with a contrast agent for visibility if required for a particular application is encapsulated within a hydrogel such as a PEG-based hydrogel. The encapsulation is accomplished by any suitable means such as mechanically combining the tissue marker and sealant in a mold, by compression, and the like. The hydrogel part of the combined polymer is dehydrated and delivered to the target site. Hydration of the polymer causes its expansion and thus provides a mechanical anchoring of the implant in the tissue. These properties are attained by combining the teachings of the first and second-incorporated disclosures. Where the polymer is used as a tissue marker, it is molded or extruded into different shapes to provide anchoring properties.

The contrast agent, if provided, is also accompanied by or replaced with different pharmaceutical agents such as anticancer drugs, antibiotics, anti-inflammatory drugs and the like that are slowly released using PGA/PLA/PCL/PDO substrates of the first-incorporated disclosure while the hydrogels of the second-incorporated disclosure provides a suitable anchoring means. The degradation of the external hydrogel may also be tailored to have a prolonged degradation time while the PGA/PLA/PCL/PDO combined with a drug agent could be degraded at a faster rate.

Examples of suitable bioabsorbable materials that expand when contacted by water include hydrogels, collagen, polysalactic acid, and any other suitable hydrophilic agents.

Examples of polymers that swell in the presence of aqueous fluids such as biological fluids will now be disclosed. Virtually all of the following polymers are hydrogels. Synthetic hydrogels can be prepared from the following classes of polymers and these are generally considered to be non-biodegradable: poly (hydroxyalkyl methylacrylates) such as poly(glyceryl methacrylate)poly(acrylamide) and poly (methacrylamide) and derivativespoly(N-vinyl-2-pyrrolidone)anionic and cationic hydrogelspoly(vinyl alcohol)poly (ethylene glycol) diacrylate and derivatives from block copolymers composed of poly(ethylene oxide)-poly(propylene oxide)-poly(ethylene oxide) and poly(propylene oxide)-poly(ethylene oxide)-poly(propylene oxide) blocks, respectively; All of the above can be cross-linked with agents such as ethylene glycol dimethacrylate or methylene-bis-acrylamide.

Biodegradable synthetic hydrogels can be prepared from polymers such as those listed above by incorporating one or more of the following monomers: Glycolide, Lactide, e-Caprolactone, p-Dioxanone and Trimethylene CarbonateIn addition, biodegradable hydrogels can be based on natural products such as the following: Polypeptides such gelatin which may be cross-linked with formaldehyde or glutaraldehyde and various other dialdehydes.

Modified chitin hydrogels, which may be prepared from partially N-deacetylated chitin which, may then be cross-linked with agents such as glutaraldehyde.

Dextran, a polysaccharide, can be derivatized with groups such as 3-acryloyl-2-hydroxypropyl esters and subsequently cross-linked by free radical copolymerization with N',N'-methylenebisacrylamide.

Starch may be similarly derivatized or using glycidyl acrylate followed by free radical cross-linking as described above.

The plug is impregnated with a contrasting agent to facilitate detection of the plug by imaging means selected from the group of imaging means consisting of magnetic resonance imaging, ultrasound, Doppler, and roentgenological means including x-ray, CT scan, mammography, and fluoroscopy.

Suitable contrast agents include a colored substance such as a dye or colorant such as methylene blue, gentian violet, indigo, dyes used in tattooing or colorant particles such as India, indigo, carbon particles or carbon preparations described in Langlois, S. L. P. and Carter, M. L. *Carbon Localization of Impalpable Mammographic Abnormalities*, Australis Radiol. 35:237-241 (1991) and/or Svane, G. A. *Stereotaxis Technique for Preoperative Marking of Non-Palpable Breast Lesions*, Acta Radiol. 24 (2): 145-151 (1983). Chemical compounds that serve as suitable contrast agents include AgCl, AgI, $BaCO_3$, $BaSO_4$, K, $CaCO_3$, ZnO, $Al_2O_3$, $AGNO_3$, ammonium salts, sodium salts, potassium salts, ethiodized oil, isohexol, isopamidol, gas, lipid, oil, and all possible combinations thereof. Alternatively, the plug includes a radioactive substance detectable by a radiation detecting means including a gamma counter and a scintillation counter. In another alternative, the plug includes a transmitting means adapted to transmit signals in the electromagnetic spectrum that are detectable by receivers adapted to receive signals in the electromagnetic spectrum.

This invention further includes the fabrication of tubular implants for implanting in tubular organs. Such a structure includes a lumen defined by a PGA/PLA/PCL/PDO polymer and a hydrogel that provides the exterior of the implant. Thus, as the hydrogel expands upon contact with a liquid fluid, it anchors itself into the surrounding tissue. The inner layer of the hydrogel contains a circular solid polymer made of PGA/PLA/PCL/PDO as a structural support to maintain an open lumen. The lumen remains open even when the hydrogel has fully expanded because the expansion is radially outward, away from the PGA/PLA/PCL/PDO polymer substrate that defines the lumen. A drug or drugs may be added to the polymer substrate so that said drug or drugs are delivered over time to the patient as the substrate degrades. As mentioned above, in most cases the polymer substrate is designed to degrade at a rate faster than the degradation rate of the hydrogel cover.

The primary object of this invention is to provide a combination tissue marker and sealant that prevents migration of the marker.

Another important object is to provide biodegradable polymers that perform the functions of marking a site, delivering drugs or other therapeutic agents to a site, and sealing openings or tracts left by a biopsy procedure or other surgical procedure.

Another object is to provide a hydrophobic coating that extends the degradation rate by shielding the substrate from moisture or bodily fluids for a predetermined time.

Another important object is to provide a combination tissue marker and sealant that does not require in-situ curing.

Yet another important object is to encapsulate a tissue marker in a sealant material that is more compatible to soft tissue than is a tissue marker.

These and other important objects, advantages, and features of the invention will become clear as this description proceeds.

The invention accordingly comprises the features of construction, combination of elements, and arrangement of parts that will be exemplified in the description set forth hereinafter and the scope of the invention will be indicated in the claims.

BRIEF DESCRIPTION OF DRAWINGS

For a fuller understanding of the nature and objects of the invention, reference should be made to the following detailed description, taken in connection with the accompanying drawings, in which:

FIG. 14 is a diagrammatic view of the marker and sealant combination when used in a biliary tract; and FIG. 15 is a diagrammatic view of the marker and sealant combination when used in a fallopian tube.

DETAILED DESCRIPTION

Figure 1A:
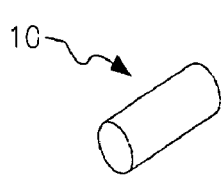
FIG. 1A is a perspective view diagrammatically depicting the tissue marker material in the form of a solid rod. It may also be interpreted as depicting said tissue marker material in the form of a hollow cylinder.

How to achieve non-covalent bonding of ionic and non-ionic contrast agent with polymers such as PGA/PLA/PCL/PDO will now be described. Different techniques are employed to accomplish similar results in connection with covalent bonding.

The starting materials employed in this invention for synthesizing the novel tissue marker include poly(DL-lactide), inherent viscosity (IV) of 0.63 dL/g (where the solvent is $CHCl_3$ and the concentration is approximately 0.5 g/dL at 30° C.), 50/50 poly(DL-lactide-co-glycolide), IV of 0.17 dL/g (hexafluoroisopropanol, concentration ~0.5 g/dL at 30° C.) and 75/25 poly(DL-lactide-co-glycolides), having IVs of 0.44 dL/g ($CHCl_3$, concentration ~0.5 g/dL at 30° C.) and 0.69 dL/g ($CHCl_3$, concentration ~0.5 g/dL 30° C.). These materials are commercially available from Birmingham Polymers, Inc., of Birmingham, Ala.

Further starting materials for synthesis of the novel tissue marker include poly (DL-lactide), IV of 1.6 dL/g ($CHCl_3$, concentration 0.1% at 25° C.), commercially available from Boehringer Ingelheim of Petersburg, Va., under the trademark RESOMER® R 207. Contrast agents sodium diatrizoate and 5-(N-2,3-dihydroxypropylacetamido)-2,4,6-triiodo-N,N'-bis (2,3-dihydroxypropyl) isophthalamide (iohexol) is commercially available from Sigma Chemical Co. of Milwaukee, Wis. Glycolide and DL-lactide monomers are commercially available from Purac America Inc. of Lincolnshire, Ill. 1-Dodecanol and ε-caprolactone are commercially available from Aldrich Inc. of Milwaukee, Wis. Tin (II) 2-ethylhexanoate is commercially available from Air Products and Chemicals, Inc. of Allentown, Pa. DL-lactic acid (JT Baker reagent) is commercially available from VWR Scientific of Bridegeport, N.J. Solvents such as tetrahydrofuran (THF), toluene, methanol, and hexanes of reagent grade or better are commercially available from multiple well-known sources.

As a first example, synthesis of 75/25 poly(DL-lactide-co-ε-caprolactone) copolymer, hereinafter referred to as 75/25 DL-PLCl, is performed by charging 22.5 grams of ε-caprolactone, 310 mls of toluene, 0.422 grams in 3.02 mls of tolulene solution of 1-dodecanol and 0.382 grams in 2.34 mls of tolulene solution of stannous octoate catalyst into a one liter, three neck, round bottom flask. The reaction solution is placed in an argon atmosphere, stirred with an overhead stirrer that includes a glass stirrer shaft equipped with a Teflon® blade and approximately 100 mls of the solvent is distilled off at atmospheric pressure. The reaction temperature is lowered to approximately 90° C. and 67.5 grams of solid DL-lactide is added to the solution in one portion. The reaction temperature is raised to approximately 110° C. to afford a gentle reflux. After forty eight hours at that temperature, heating is discontinued and the reaction solution temperature is allowed to fall to 75°. The solution is diluted with 600 mls of toluene and stirred at 55-60° for 1.5 hours. The diluted reaction solution is transferred into a crystallizing dish and the polymer is precipitated with one liter of hexanes. The supernatant is then decanted off and the viscous residue dried for one to three days under a vacuum at 40° C. to a constant weight. The solid polymer is removed from the dish and stored under an argon atmosphere at 30° C.

Synthesis of 20/80 poly(DL-lactite-co-ε-caprolactone), hereinafter referred to as 20/80 DL-PLCl and 10/90 poly (glycolide-co-ε-caprolactone), hereinafter referred to as 10/90 PGCl copolymers are prepared by the same process used for the preparation of 75/25 DL-PLCl in the first example, with the exception that, in the case of the 20/80 DL-PLCl copolymer, DL-lactic acid is used as the initiator instead of 1-dodecanol. The contents of each monomer in the final purified polymers are determined by high resolution proton nuclear magnetic resonance spectroscopy and these are summarized in Table 1. That table further includes the melting points for 20/80 DL-PLCl and 10/90 PGCl copolymers, which are obtained by differential scanning calorimetry (DSC).

TABLE 1

Chemical and Physical Properties of the Synthesized Polymers

| Polymer | Copolymer Composition Glycolide | Copolymer Composition DL-Lactide | Weight % ε-Caprolactone | Melting Point °C. | Mol. Wt. Mn 1 |
|---|---|---|---|---|---|
| 20/80 DL-PLC1 | — | 20 | 80 | 46 | 40-70K |
| 75/25 DL-PLC1 | — | 75 | 25 | Amorphous | 20-30K |
| 10/90 PGC1 | 9.4 | — | 90.6 | 55 | 30-60K |

Molecular weights were determined by GPC using methylene chloride solvent and polystyrene standards.

In a third example, the 75/25 poly(DL-lactide-co-glycolide) with iohexol is formulated by preparing a 2% by weight over volume solution of the iohexol contrast agent by mixing 5.15 grams of the solid contrast agent in 130 mls of methanol in a 500 ml Erlenmeyer flask for 5-10 minutes until the solid is fully dissolved. The solution is then diluted with 130 mls of tetrahydrofuran (THF) to provide the 2% solution. A 6% solution of the biodegradable polymer is prepared in a one liter Erlenmeyer flask by addition of 330 mls of THF to 20.6 grams of the solid 75/25 DL-PLG polymer. The mixture is stirred with gentle heating (30-40° C.) until the solid is dissolved. The entire contrast solution is then slowly poured into the stirred polymer solution to give a single-phase solution of the polymer and the contrast agent. The combined solution is stirred for an additional five minutes and then the polymer and contrast agent are co-precipitated with hexanes. The precipitation is achieved by rapid addition of two volumes of hexanes to a rapidly mixed solution of the polymer/contrast solution. The mixture is again stirred for an additional five minutes and then allowed to sit unstirred at room temperature for five to ten minutes to allow the solid to settle to the bottom of the flask. The supernatant is then decanted and discarded and the semi-solid residue is dried under vacuum for one to two days at 40° C. to a constant weight. Quantitative recovery of 100.8% of the solids is obtained for the polymer and the contrast agent in this example. The solid, which is used for fabrication of the novel markers, contains 20% by weight of contrast agent as a homogenous mixture with the biodegradable polymer.

To study the effect of the contrast agent content in the biodegradable markers on their visualization under X-ray imaging, two different DL-PLG polymers are formulated with the iohexol contrast agent in which the contrast is varied between 5 and 40% by weight. These markers are formulated by a procedure similar to the procedure for the marker prepared in the third example. The composition of these biodegradable marker solids is summarized in Table 2. The recovery of the solids after the hexanes precipitation step is greater than 97% for all of the marker compositions listed in Table 2.

TABLE 2

Compositions of the Biodegradable Markers

| Polymer | Source and Inherent Viscosity Lot # | Source and Inherent Viscosity DL/g | Contrast Agent Type | Contrast Agent Name | Contrast Content % (w/w) |
|---|---|---|---|---|---|
| 50/50 DL-PLG | BPID00120 | 0.17 | Non-ionic | Iohexol | 5 |
| 50/50 DL-PLG | BPID00120 | 0.17 | Non-ionic | Iohexol | 10 |
| 50/50 DL-PLG | BPID00120 | 0.17 | Non-ionic | Iohexol | 20 |
| 50/50 DL-PLG | BPID00120 | 0.17 | Non-ionic | Iohexol | 30 |
| 50/50 DL-PLG | BPID00120 | 0.17 | Non-ionic | Iohexol | 40 |
| 75/25 DL-PLG | BPID98054 | 0.44 | Non-ionic | Iohexol | 5 |
| 75/25 DL-PLG | BPID98054 | 0.44 | Non-ionic | Iohexol | 10 |

The contrast solution may also be an ionic contrast solution such as sodium diatrizoate, for example.

The novel biomarkers may be fabricated by extrusion, injection molding, or compression molding. Multiple sizes and shapes may be fabricated using these or similar manufacturing processes. By controlling pressure, temperature, and extrusion speed rate during the extrusion process, differing sizes and properties are obtainable. During the development of this invention, different extrusion and compression molding processes were used to fabricate the markers.

The novel biomarkers and the novel sealant material may be combined in a variety of fabrication processes. During the development of this invention, insert molding was used to combine the marker and the sealant to one another. Different sizes and shapes having differing properties may be manufactured using insert injection and compression molding, for example.

To extend the biodegradable marker's range of properties such as degradation times, ability to be visualized under ultrasound, hardness and fabrication temperatures, marker solids are prepared from additional types of polymers with both ionic and non-ionic contrast agents as indicated in Table 3. Most of these biodegradable markers are formulated with 20% contrast agent. The recovery of the solids after the hexanes precipitation step is greater than 91% in all of these formulations.

TABLE 3

Compositions of the Biodegradable Markers [t3]

| Polymer | Source and Inherent Viscosity Lot # | Source and Inherent Viscosity dL/g | Contrast Agent Type | Contrast Agent Name | Contrast Content % (w/w) |
|---|---|---|---|---|---|
| DL-PLA | BI260911 | 1.6 | Ionic | Sodium Diatrizoate | 10 |
| DL-PLA | BI260911 | 1.6 | Ionic | Sodium Diatrizoate | 20 |
| DL-PLA | BI260911 | 1.6 | Non-ionic | Iohexol | 10 |
| DL-PLA | BI260911 | 1.6 | Non-ionic | Iohexol | 20 |
| DL-PLA | BPID00004 | 0.63 | Non-ionic | Iohexol | 20 |
| PGC1 | See Example 3 | — | Non-ionic | Iohexol | 20 |
| 20/80DL-PLC1 | See Example 3 | — | Non-ionic | Iohexol | 20 |
| 20/80DL-PLC1 | See Example 3 | — | Ionic | Sodium Diatrizoate | 20 |
| 75/25DL-PLC1 | See Example 3 | — | Non-ionic | Iohexol | 20 |

The type of polymer used can be any of the biodegradable polymers such as other PLGA polymers, e.g., 50/50 DL-PLGA, 50/50 L-PLGA, etc., or the L-PLCl, PGCl, etc.

The contrast agent can be formulated in these polymers at any concentration ranging from 0 to 50% by weight, but preferably at 70% by weight. (That statement contradicts itself.

The solvent combinations can also be varied as well as the precipitation methods.

There are many applications for the novel implants. For example, during diagnosis of hepatic carcinoma or other hepatic disease using a liver biopsy under CT visualization, a biopsy tract is formed. The tract may be plugged to prevent bleeding by using the above-mentioned PGA/PLA/PCL/PDO based polymer combined with a contrast agent for visibility and encapsulated within a hydrogel. Drugs or any other pharmaceutical agents could be delivered to the liver by replacing the contrast agent with such drugs or agents.

As another example, a heart biopsy may be conducted near diseased heart tissue using a mechanical biopsy gun. The biopsy tract or tracts are then filled with different growth factors and stem cells to promote angiogenesis in the heart muscle tissue. One method for sealing the tract so that the stem cells and growth factor are constrained to stay in the biopsy tract for a prolonged period of time is disclosed in the second-incorporated disclosure. The present disclosure teaches the integration of two polymers where a PGA/PLA/PCL/PDO with a drug agent is encapsulated within a dehydrated hydrogel. The dehydrated hydrogel becomes hydrated within a few minutes and its expansion provides an anchoring means.

This invention also has utility in connection with prostate cancer biopsies where a biopsy needle is inserted though the rectum into the prostate gland under ultrasound visualization. Introduction into the biopsy tract of a sealing means by means of a coaxial needle will prevent leakage through the bowel into the prostate. Moreover, the plug may be used to deliver drugs or other therapeutic agents.

Similarly, the novel plugs have utility in connection with the sealing of cavities formed in a prostate gland by tissue reduction procedures undertaken after a diagnosis of BHP. Different drug agents are released over time to reduce inflammation or any other side effects.

In another application, a tubular urethral stent has a thin wall formed of a PGA/PLA/PCL/PDC/PDO polymer substrate with or without pharmaceutical agents. A layer of dehydrated hydrogel covers the thin wall but does not block the lumen of the tube. The stent is introduced into the urethra and the hydrogel expands radially outwardly, anchoring to the urethral wall. This procedure is similar to the conventional placement of a urethral stent, but it is more advantageous because it is not permanent like metallic stents and does not require in situ curing like other biodegradable stents.

The marker material that forms the inner tube also provides a drug-delivery means for the benefit of the patient.

Growth factors or pharmaceutical agents encapsulated within the novel polymers may be used advantageously in the treatment of malignant brain tumors. The combination marker and sealant of this invention has utility in the context of gene therapy treatment as the carrier for the bio-active agents and as the anchoring means to position and secure the marker to the target area.

The polymers disclosed herein are formulated to exhibit differing properties depending upon the application. Some are designed to degrade more slowly than others, some are more hydrophilic or more hydrophobic, and so on. In most applications, the contrast agent-containing polymers are formulated so that the marker is visible under X-ray and/or other imaging means for one month to six months or even longer.

Figure 1B:
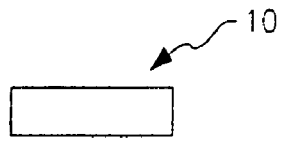
FIG. 1B is a side elevation view diagrammatically depicting the marker material in solid rod form or in hollow cylindrical form, depending upon the interpretation of the drawing.

Turning now to the drawings, FIG. 1A depicts a tissue marker made in accordance with the teachings of the first-incorporated disclosure. It is provided in the form of a solid rod 10. Its interior is filled with a contrast agent or other pharmaceutical agent. FIG. 1B depicts marker 10 in solid rod form.

Figure 1C:
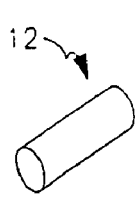
FIG. 1C is a perspective view diagrammatically depicting the sealant material in solid rod form.
Figure 1D:
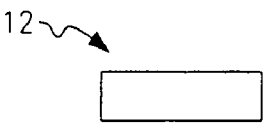
FIG. 1D is a side elevation view diagrammatically depicting the sealant material in solid rod form.

FIG. 1C depicts a hydrogel-based sealant 12 made in accordance with the teachings of the second-incorporated disclosure. In this embodiment, it is of hollow cylindrical or tubular construction and is made of hydrogels. FIG. 1D depicts sealant 12 in solid rod form.

Figure 1E:
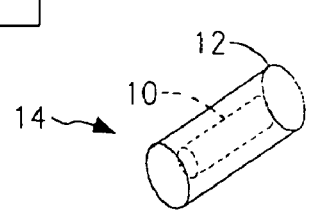
FIG. 1E is a perspective view diagrammatically depicting the marker of FIG. 1A housed within the sealant of FIG. 1C, in a rod-in-rod arrangement.
Figure 1F:
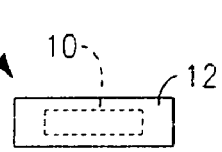
FIG. 1F is a side elevation view that diagrammatically depicts a marker of FIG. 1A or 1B encapsulated within the sealant material of FIG. 1D.

FIGS. 1E and 1F depict the basic conception behind the present disclosure which teaches the combination of marker 10 and sealant 12 of the incorporated disclosures. The combination marker and sealant member 14 of FIG. 1E has an interior 10 formed of the FIG. 1B solid rod marker and an exterior housing 12 formed of the FIG. 1C sealant. In FIG. 1E, marker 10 is co-extensive with sealant 12. In FIG. 1F, interior marker 10 is again formed in the solid rod structure of FIG. 1B, but said solid rod 10 has an extent less than that of sealant 12 so that it is encapsulated therein as depicted.

The novel combination marker and sealant member 14 is delivered to a site that requires sealing; the sealant is in dehydrated condition when delivered to the site. The sealant expands when activated by contact with water or moisture. The expansion of the hydrogel-based sealant 12 holds it in place. The contrast agent in marker 10 facilitates viewing of the site under various imaging techniques for a prolonged period of time. Marker 10 may also include therapeutic agents that are released over time as marker 10 is bioabsorbed. Hydrogels 12 are also bioabsorbed over time, but the time for such absorption is selected to exceed that of the absorption time of marker 10 if required by an application.

Figure 2A:
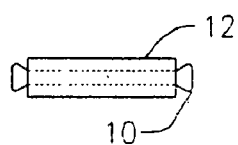
FIG. 2A is a side elevation view diagrammatically depicting the marker material formed into a dog bone shape and ensleeved within the sealant material of FIG. 1E.
Figure 2B:
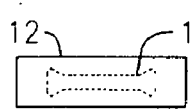
FIG. 2B is a side elevation view diagrammatically depicting the marker material of FIG. 2A encapsulated within the sealant material of FIG. 1F.

FIG. 2A depicts a marker 10 having bulbous anchoring means at its opposite ends that extend beyond the opposite ends of hydrogel housing 12. FIG. 2B depicts marker 10 having said bulbous anchoring means when fully encased within hydrogel housing 12.

Figure 3A:
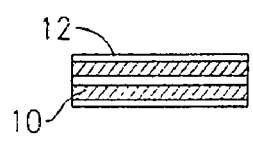
FIG. 3A is a longitudinal sectional view depicting the marker of FIG. 1A ensleeved within the sealant material of FIG. 1C in a tube-in-tube arrangement.
Figure 3B:
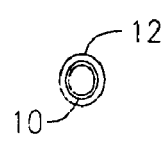
FIG. 3B is an end view of the parts depicted in FIG. 3A.

FIG. 3A is a side elevational view depicting a tube-in-tube arrangement where marker 10 is provided in tubular form and is ensleeved within sealant 12 which is also provided in tubular form. FIG. 3B provides an end view thereof.

Figure 4B:
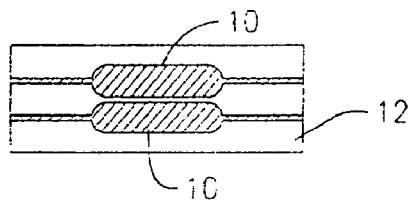
FIG. 4B depicts the parts of FIG. 4A when the sealant material is hydrated.
Figure 4A:
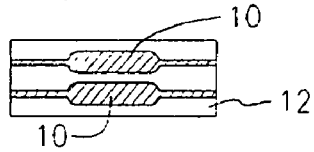
FIG. 4A is a longitudinal sectional view depicting a pair of the markers of FIG. 1A ensleeved within a double-lumened sealant material in dehydrated form.
Figure 4C:
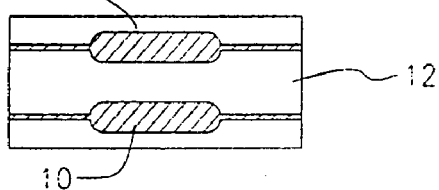
FIG. 4C is similar to FIG. 4B except it depicts the sealant material having lumens that are larger in diameter than the lumens of FIG. 4A and FIG. 4B.

Sealant 12 has a pair of open lumens in the embodiment of FIGS. 4A-C, and each of said open lumens has a marker 10 positioned therewithin. The sealant material of which outer housing 12 is formed is depicted in dehydrated form in FIG. 4A. In FIGS. 4B and 4C, the sealant has expanded due to hydration. In the embodiment of FIG. 4B, the lumen is small and in the embodiment of FIG. 4C the lumen is large.

Figure 5:
FIG. 5 is a side elevation view of a marker or sealant having a pointed distal end.

In addition to the cylindrical and rod-shaped markers 10 of FIGS. 1A and 1B, marker 10 could also be provided in the form of a rod having a pointed leading end as depicted in FIG. 5. The pointed leading end could serve as an anchoring means that prevents migration of marker 10 from its intended location.

Figure 6:
FIG. 6 is a side elevation view of a marker or sealant having a harpoon-shaped distal end.

The harpoon shape of the leading end of the marker depicted in FIG. 6 would also provide an anchoring means.

Figure 7:
FIG. 7 is a side elevation view of a marker or sealant having a "U"-shaped or clip-shaped configuration.

The embodiment of FIG. 7 provides a U-shaped tissue marker 10. This clip shape also has utility as an anchoring means. When the tissue marker is shaped such that it is self-anchoring, the hydrogel sealant is not required unless there is a need to seal a surgical or trauma-created opening.

Figure 8:
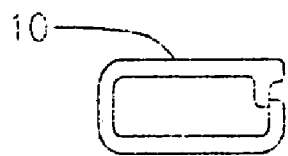
FIG. 8 is a side elevation view of a marker or sealant like that of FIG. 7 but further equipped with a latch means.

A latch means is added to the embodiment of FIG. 7 to produce the embodiment of FIG. 8. The latch means is provided to enhance the anchoring of marker 10.

Hydrogel sealant 12 may also be provided in the form of a rod, tube, pointed rod, harpoon, clip, latched clip, and the like.

Figure 9:
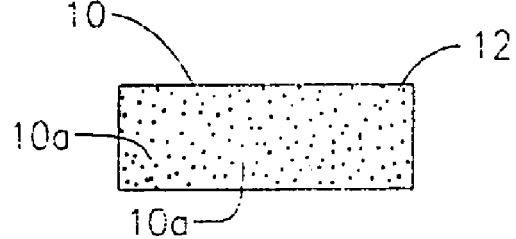
FIG. 9 is a side elevation view of a sealant having marker particles embedded therein.

Moreover, as depicted in FIG. 9, tissue marker particles, collectively denoted 10a, may be dispersed within sealant 12. Such dispersal of tissue marker particles 10a within hydrogel sealant 12 may be applied to any form of hydrogel 12. For example, marker particles 10a could be dispersed throughout a harpoon-shaped sealant 12, a "U"-shaped sealant 12, and so on.

The number of shapes is inexhaustible and these Figures are not intended to illustrate all possible shapes within the scope of this invention but are intended as exemplary only. The novel combined marker and sealant can be manufactured in any geometrical shape and size and the invention is not limited to the finite number of examples provided herein.

Six (6) examples of applications for the novel marker/sealant combination will now be disclosed.

Figure 10:
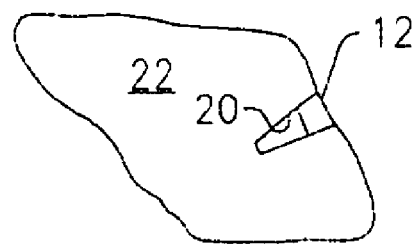
FIG. 10 diagrammatically depicts the combination marker and sealant when used to seal a liver biopsy tract.

FIG. 10 depicts a hepatic (liver) biopsy. Bore 20 is formed in liver 22 by the biopsy procedure. Plug 24 seals the bore at its surface to prevent bleeding at the biopsy site. Plug 24 may be formed of expandable sealant material 12 only so that it expands to securely seal the opening when contacted by bodily moisture, or it may include a marker 10 or marker particles 10a housed within expandable hydrogel sealant material 12. These markers have utility for viewing or drug delivery or both.

Figure 11A:
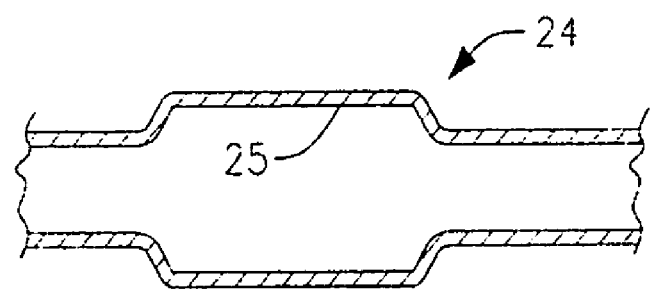
FIG. 11A is a longitudinal sectional view of an artery depicting how a section thereof is expanded by an angioplasty procedure.
Figure 11B:
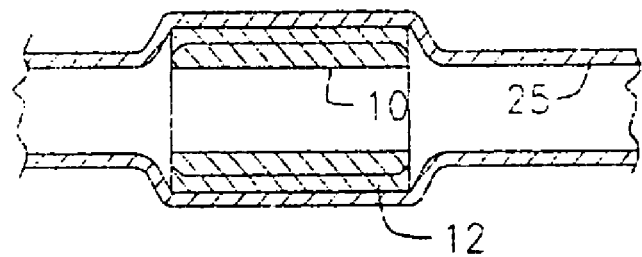
FIG. 11B is a view like FIG. 11A and adds a longitudinal sectional view of the combination marker and sealant of this invention positioned in said expanded section of said artery.

A diagrammatic longitudinal sectional view of an expanded artery after an angioplasty procedure is denoted 24 in FIG. 11A. Hydrogel sealant 12, in tubular form, is initially positioned within lumen 25 of the artery in unhydrated form; it then expands to the position depicted in FIG. 11B to hold the artery open. Marker material 10, also in tubular form, is positioned radially inwardly of sealant 12 and provides support therefor.

Figure 11C:
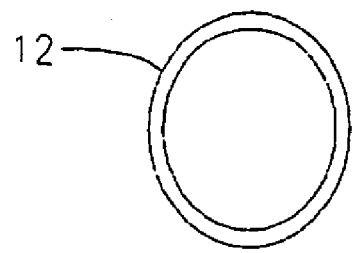
FIG. 11C is a cross-sectional view of the sealant when hydrated and in annular form.
Figure 11D:
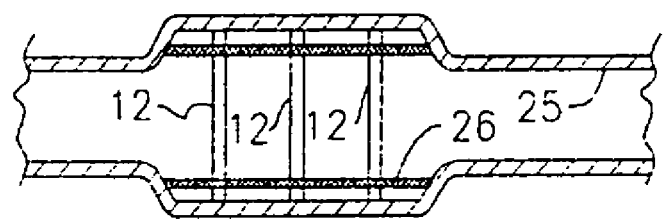
FIG. 11D is a view like FIG. 11A and depicts a plurality of the ring-shaped sealants of FIG. 11C disposed in supporting relation to said expanded area of said artery, said sealants being used in conjunction with a metallic stent.

In the alternative, expandable sealant material 12 may be provided in annular, i.e., ring form as depicted in FIG. 11C and a plurality of said rings may be disposed in longitudinally and equidistantly spaced relation to one another along the extent of the expanded section of artery, in transverse relation to the longitudinal axis of the artery, as indicated in FIG. 11D.

Figure 11E:
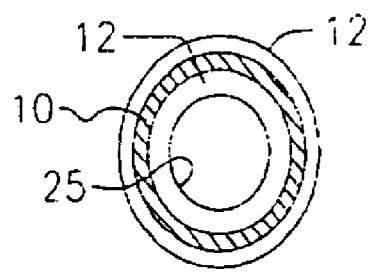
FIG. 11E is an end view depicting a tube-in-tube-in-tube arrangement where the marker of FIG. 1A ensleeves a first sealant of tubular configuration and is ensleeved by a second sealant of tubular configuration having a diameter larger than the diameter of the first sealant.

Moreover, as depicted in FIG. 11E, marker material 10 in annular form may be sandwiched between inner and outer layers of sealant material 12. Where the bioabsorbable marker material contains a contrast agent, the location of the site is made apparent under imaging for a prolonged period of time. Where therapeutic agents are contained within the marker material, a time-release of said agents is provided as the marker material is slowly bioabsorbed.

Figure 12A:
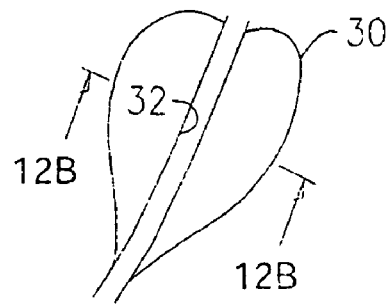
FIG. 12A is a diagrammatic view of a prostate gland and a urethra.
Figure 12B:
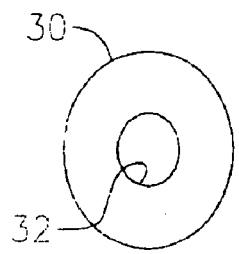
FIG. 12B is a sectional view taken along line 12B-12B in FIG. 12A.
Figure 12C:
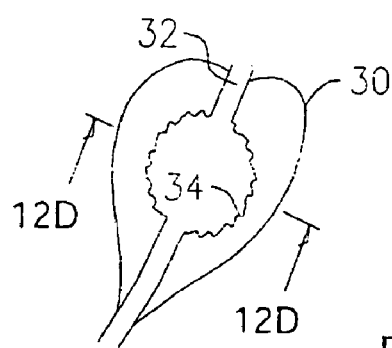
FIG. 12C is a diagrammatic view of the prostate gland of FIG. 12A after a tissue reduction procedure has been performed.
Figure 12D:
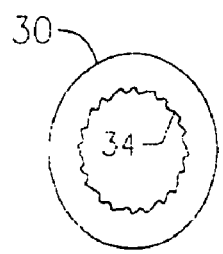
FIG. 12D is a sectional view taken along line 12D-12D in FIG. 12C.
Figure 12E:
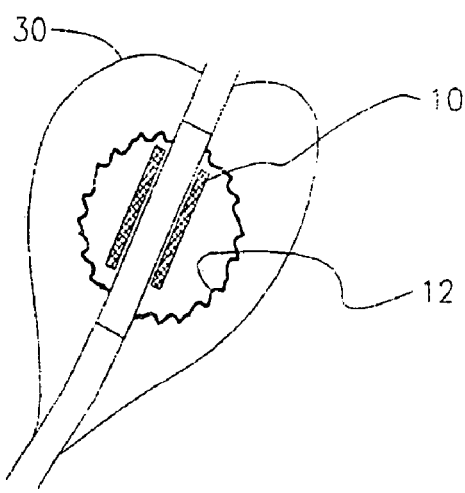
FIG. 12E is a diagrammatic view like that of FIG. 12C, depicting the combination marker and sealant positioned in structural support relation to the excised part of the gland.

Still another application for the novel combination of materials is depicted in FIGS. 12A-F. FIG. 12A diagrammatically depicts a prostate gland 30 and a urethra 32 in perspective and FIG. 12B provide s a diagrammatic cross-sectional view thereof. If gland 32 is enlarged, a condition known as BHP, it can compress the urethra and cause a restricted urine flow. As indicated in FIG. 12C, the condition is surgically treated by removing the part of gland 30 that is applying pressure to urethra 32; the resulting opening is denoted 34 in FIGS. 12C and 12D. FIG. 12E indicates how a tubular-in-configuration marker 10 is housed within a tubular-in-configuration sealant 12 to provide support for said sealant and to provide a slow delivery of therapeutic agents to the surgical site. The moisture-activated expansion of sealant 12 anchors it to urethra 32 and to prostate gland 30. The urethra is usually damaged during TURP. The lumen serves as a temporary urethra until the prostate grows back.

Figure 13:
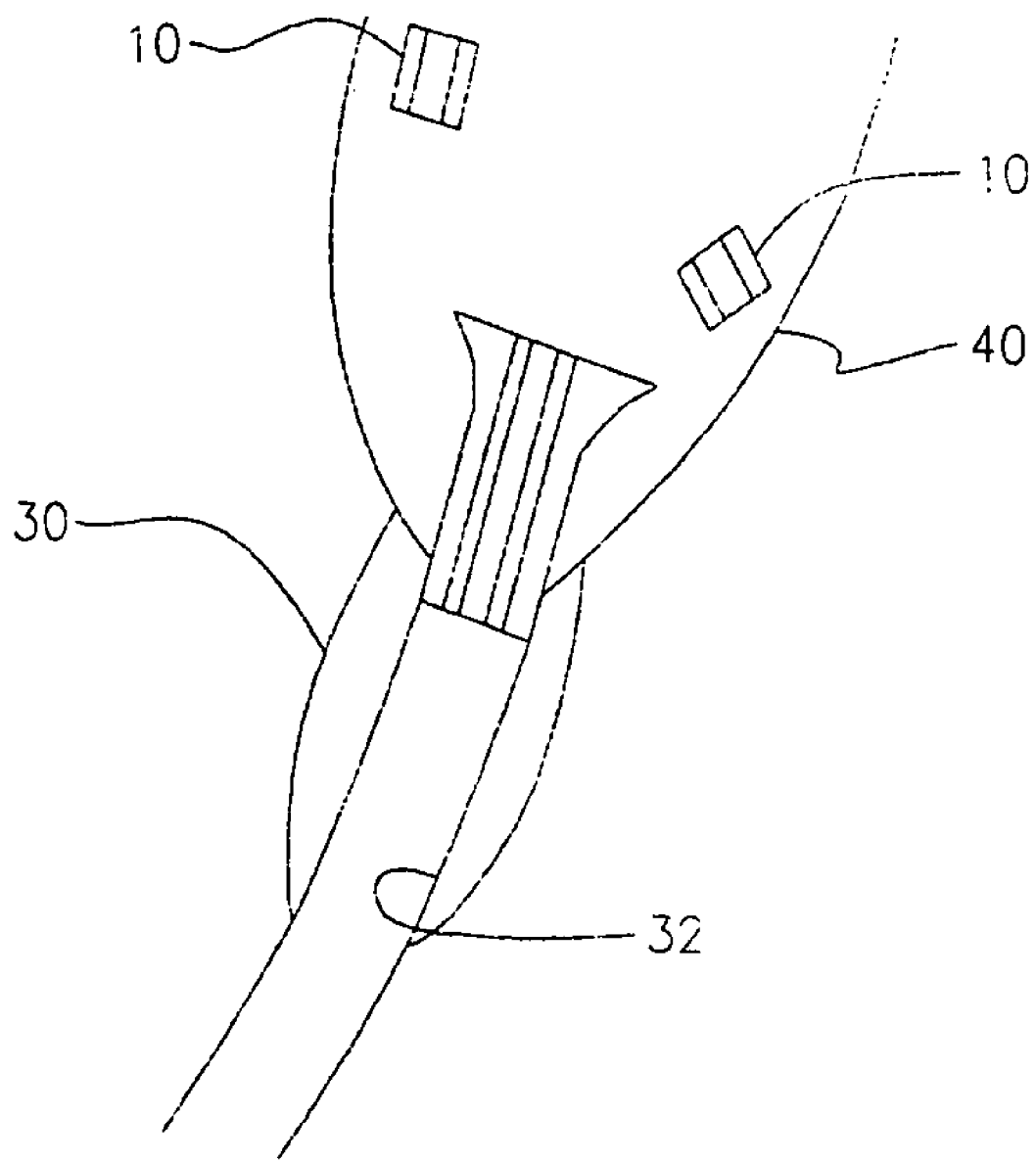
FIG. 13 is a diagrammatic view of the marker and sealant combination when positioned at the juncture of a bladder and a urethra.

FIG. 13 depicts an application where drugs or other pharmaceutical agents are delivered to a bladder 40. This is a tube-in-tube-in-tube arrangement where a first tubular section of sealant material 12 is entubed within a tubular section of marker material 10 which is entubed within a second section of sealant material 12. The structure in dehydrated condition is positioned at the neck of bladder 40 where it joins urethra 32. Upon activation, sealant material 12 expands to secure the marker 10 in position. As sealant 12 is bioabsorbed, drugs for treatment of bladder disease are released from said sealant 12 and administered to the bladder. Pharmaceutical agents of smaller molecular size could be carried by bioabsorbable marker 10.

The novel sealant, when hydrated, makes the site more visible under ultrasound.

FIG. 14 depicts a biliary tract 50 where an opening therein is sealed by the structure depicted in FIGS. 3A and 3B, i.e., tubular marker 10 is housed within tubular sealant 12 in a tube-in-tube arrangement. The open lumen of marker 10 enables fluid to flow through the structure. As in the other embodiments, sealant 12 expands in response to contact with moisture to hold the tube-in-tube structure in position and marker 10 contains either contrast agent or therapeutic agents, or both, for gradual release as the tube-in-tube structure biodegrades.

The same tube-in-tube structure may be used to seal openings in fallopian tubes 60a, 60b, as diagrammatically depicted in FIG. 15.

The invention is not limited to liver, artery, prostate gland, bladder, biliary tract and fallopian tube applications. In view of these exemplary applications, other applications will become apparent to those of ordinary skill in the medical arts. Expandable sealant material 12 has utility in sealing any opening and in providing an anchoring means for the marker material even if no sealing is required. The marker material may contain a contrast agent or a therapeutical agent, or both, that are released over time as the marker is bioabsorbed.

It will thus be seen that the objects set forth above, and those made apparent from the foregoing description, are efficiently attained. Since certain changes may be made in the above construction without departing from the scope of the invention, it is intended that all matters contained in the foregoing description or shown in the accompanying drawings shall be interpreted as illustrative and not in a limiting sense.

It is also to be understood that the following claims are intended to cover all of the generic and specific features of the invention herein described, and all statements of the scope of the invention that, as a matter of language, might be said to fall therebetween.

What is claimed is:

1. An implant for insertion into a lumen or void during a surgical procedure comprising:
    a polymer plug and
    a sealant covering at least a portion of the polymer plug, wherein the sealant comprises a hydrogel and anchors the implant against migration after insertion into the lumen or void.

2. The implant of claim 1, wherein the sealant ensleeves the polymer plug.

3. The implant of claim 1, wherein the sealant completely encapsulates the polymer plug.

4. The implant of claim 1, wherein the sealant expands when contacted by water.

5. The implant of claim 1, wherein the hydrogel comprises a biodegradable monomer selected from the group consisting of glycolide, lactide, c-caprolactone, p-dioxanone, trimethylene carbonate, and mixtures thereof.

6. The implant of claim 1, wherein the hydrogel comprises a non-biodegradable polymer selected from the group consisting of poly(hydroxyalkyl methylacrylates), poly(acrylamide), poly(methacrylamide), poly(N-vinyl-2-pyrrolidone), anionic hydrogels, cationic hydrogels, poly(vinyl alcohol), poly(ethylene glycol) and its derivatives, and mixtures thereof.

7. The implant of claim 1, wherein the polymer plug has a cylindrical cross section.

8. The implant of claim 1, wherein the polymer plug has an annular cross section.

9. The implant of claim 1, wherein the polymer plug comprises poly(lactide), poly(glycolide), poly(caprolactone), poly(dioxanone), poly(ethylene glycol), collagen, gelatin, copolymers of the foregoing, and mixtures of the foregoing.

* * * * *